US011974729B2

(12) United States Patent
McGrath

(10) Patent No.: US 11,974,729 B2
(45) Date of Patent: *May 7, 2024

(54) VIDEO LARYNGOSCOPE

(71) Applicant: Covidien AG, Neuhausen (CH)

(72) Inventor: Matthew John Ross McGrath, Edinburgh (GB)

(73) Assignee: Covidien AG (CH)

(*) Notice: Subject to any disclaimer, the term of this patent is extended or adjusted under 35 U.S.C. 154(b) by 521 days.

This patent is subject to a terminal disclaimer.

(21) Appl. No.: 17/212,822

(22) Filed: Mar. 25, 2021

(65) Prior Publication Data
US 2021/0275008 A1  Sep. 9, 2021

Related U.S. Application Data

(63) Continuation of application No. 16/294,163, filed on Mar. 6, 2019, now Pat. No. 10,973,401, which is a
(Continued)

(30) Foreign Application Priority Data

May 13, 2010  (GB) ..................... 1008022
Sep. 23, 2010  (GB) ..................... 1016011

(51) Int. Cl.
A61B 1/267  (2006.01)
A61B 1/00  (2006.01)
A61B 1/05  (2006.01)

(52) U.S. Cl.
CPC .......... *A61B 1/267* (2013.01); *A61B 1/00052* (2013.01); *A61B 1/00066* (2013.01); *A61B 1/05* (2013.01)

(58) Field of Classification Search
CPC . A61B 1/267; A61B 1/00052; A61B 1/00045; A61B 1/00048; A61B 1/00066; A61B 1/05
(Continued)

(56) References Cited

U.S. PATENT DOCUMENTS 4,947,896 A * 8/1990 Bartlett ................ A61B 1/0623
600/187
5,827,178 A  10/1998 Berall
(Continued)

FOREIGN PATENT DOCUMENTS

CN  200951074  9/2007
DE  10351155  6/2005
(Continued)

OTHER PUBLICATIONS

International Search Report for PCT/GB2010/151729, dated May 11, 2011, 2 pages.
(Continued)

*Primary Examiner* — Tessa M Matthews
*Assistant Examiner* — David C Comstock

(57) ABSTRACT

Disclosed is a video laryngoscope having a body, an insertion section extending from the body generally parallel to a median plane of the laryngoscope extending through the body, and a display screen assembly extending from the body generally perpendicular to the median plane, the body having a grip portion intermediate the display screen assembly and the insertion section. The display screen assembly, including a display screen, extends laterally from the body and the inner edge of the display screen falls within the lateral extent of the body. The display screen may be adjustable about an axis.

20 Claims, 12 Drawing Sheets

Related U.S. Application Data continuation of application No. 15/911,883, filed on Mar. 5, 2018, now Pat. No. 10,617,292, which is a continuation of application No. 15/147,371, filed on May 5, 2016, now Pat. No. 9,907,464, which is a continuation of application No. 13/697,651, filed as application No. PCT/GB2010/051729 on Oct. 13, 2010, now Pat. No. 9,364,140.

(58) Field of Classification Search
USPC .......................................... 600/185, 188, 197
See application file for complete search history.

(56) References Cited

U.S. PATENT DOCUMENTS

| | | | |
|---|---|---|---|
| 5,829,099 A * | 11/1998 | Kopelman | B25G 1/102 16/430 |
| 5,846,186 A | 12/1998 | Upsher | |
| 8,366,612 B2 | 2/2013 | Rosenthal | |
| 9,364,140 B2 | 6/2016 | McGrath | |
| 9,820,642 B2 | 11/2017 | Law et al. | |
| 9,907,464 B2 * | 3/2018 | McGrath | A61B 1/00052 |
| 10,973,401 B2 * | 4/2021 | McGrath | A61B 1/267 |
| 2002/0022769 A1 | 2/2002 | Smith et al. | |
| 2003/0195390 A1 | 10/2003 | Graumann | |
| 2005/0059863 A1 | 3/2005 | Zilch | |
| 2006/0106122 A1 | 5/2006 | Naito et al. | |
| 2007/0106122 A1 | 5/2007 | Yokota et al. | |
| 2008/0064926 A1 | 3/2008 | Chen | |
| 2008/0177148 A1 | 7/2008 | Chen et al. | |
| 2008/0312507 A1 | 12/2008 | Kim | |
| 2010/0095487 A1 * | 4/2010 | Gitman | B43K 23/008 16/430 |
| 2011/0306839 A1 * | 12/2011 | Young | A61B 1/267 600/188 |
| 2012/0178999 A1 | 7/2012 | Takeda et al. | |

FOREIGN PATENT DOCUMENTS

| | | |
|---|---|---|
| JP | 20050218644 | 8/2005 |
| JP | 20060326111 | 7/2006 |
| JP | 20060229906 | 8/2006 |
| JP | 20070144123 | 6/2007 |
| JP | 20110055941 | 3/2011 |
| WO | 20090027672 A1 | 3/2009 |
| WO | 20110066510 A2 | 6/2011 |

OTHER PUBLICATIONS

Office Action (5 pgs.) dated Mar. 4, 2014, issued in corresponding Japanese Application No. 2013-509606 with an at east partial English-language translation thereof (7 pgs.).

* cited by examiner

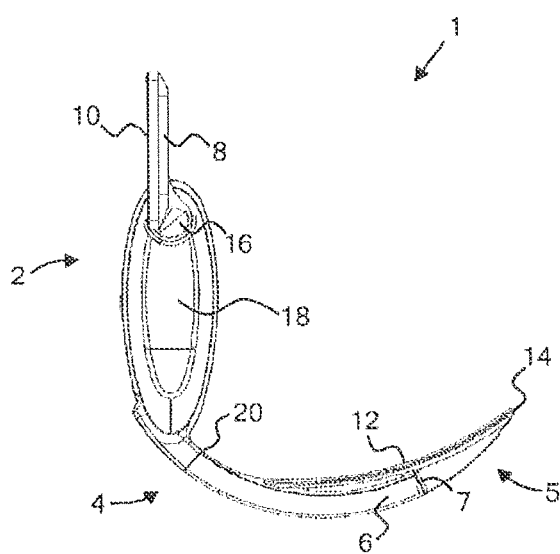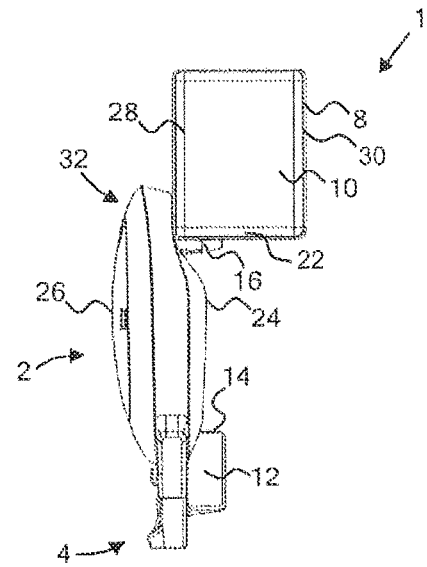
Fig. 1a　　　Fig. 1b
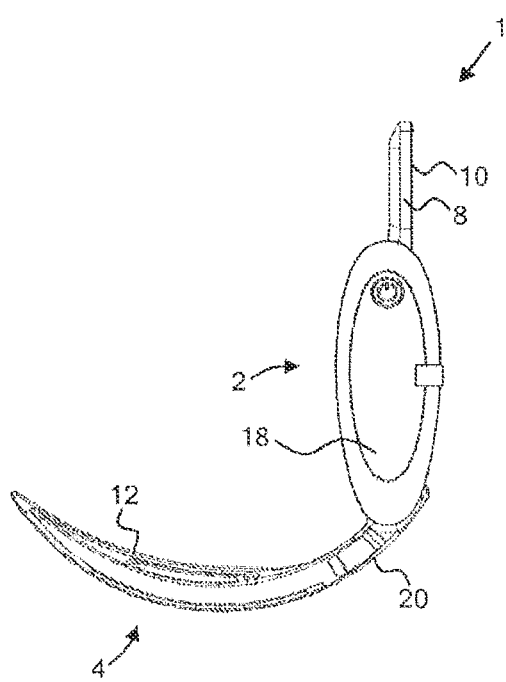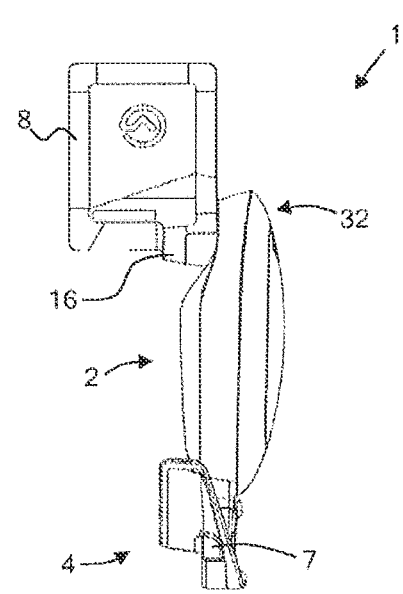
Fig 1c　　　Fig. 1d

VIDEO LARYNGOSCOPE

CROSS-REFERENCE TO RELATED APPLICATIONS

This application is a continuation of U.S. application Ser. No. 16/294,163 filed Mar. 6, 2019, entitled "Video Laryngoscope," which is a continuation of U.S. application Ser. No. 15/911,883 filed Mar. 5, 2018, entitled "Video Laryngoscope," which is a continuation of U.S. patent application Ser. No. 15/147,371 filed May 5, 2016, entitled "Video Laryngoscope," now U.S. Pat. No. 9,907,464 which issued on Mar. 6, 2018, which is a continuation of U.S. application Ser. No. 13/697,651 filed Nov. 13, 2012, entitled "Video Laryngoscope," now U.S. Pat. No. 9,364,140 which issued on Jun. 14, 2016, which is the United States national stage of International Application No. PCT/GB2010/051729 filed Oct. 13, 2010, entitled "Video Laryngoscope," which claims the benefit of Great Britain Application No. 1016011.7 filed Sep. 23, 2010, entitled "Video Laryngoscope," and Great Britain Application No. 1008022.4 filed May 13, 2010, entitled "Video Laryngoscope," which are all incorporated by reference herein in their entirety for all purposes.

FIELD OF THE INVENTION

The present invention relates to the field of video laryngoscopes having video screens which are either integral to, or demountably attachable to, the body of the video laryngoscope.

BACKGROUND TO THE INVENTION

Laryngoscopes have been in use for a very long period of time to enable a view to be obtained of the larynx, and to lift tissue adjacent to the epiglottis, or to lift the epiglottis directly, to enable an endotracheal tube to be inserted into a patient's trachea. The first laryngoscopes were direct laryngoscopes, enabling a user to obtain a direct line of sight to the patient's trachea, and direct laryngoscopes are typically straight, curved or angled. Indirect laryngoscopes include a viewing device to enable an indirect view of the trachea to be provided to a user. Early indirect laryngoscopes used a prism, lenses or a series of reflecting mirrors. Later, fibre-optics devices were employed and then video cameras were mounted on the laryngoscope blade (the part which extends into a patient's oral cavity in use) once they became sufficiently small and cost-effective.

Within this specification and the appended claims, by a video laryngoscope, we refer to laryngoscopes including a video camera for obtaining a view before or during the intubation process. Video laryngoscopes may include a video camera as part of the blade. Alternatively, they may include a fibreoptic arrangement which conducts light from a suitable viewing position to a video camera location on the blade or in another part of the laryngoscope, such as the handle, or conceivably remotely from the laryngoscope. By a video display region we refer to a surface area on which video images are shown, excluding boundaries, supports etc.

Video laryngoscopes are known which output video signals to a remote display through a wired or wireless video output interface. The present invention relates to those which include a display for displaying video images obtained from the video camera. The display may be permanently mounted to the laryngoscope, or demountable.

Video laryngoscopes typically have both a handle and a blade, which may be separable or integral to each other. The handle may be at any of a range of angles to the blade, such as around 90°, or generally coaxial with the blade. Blades can be curved, straight and include one of more bends, which may be defined or arise from the smooth changes in curvature. In each case, the term distal is used within this specification and the appended claims to refer to the end of the device which extends furthest towards the larynx in use—typically the end of the blade, and the term proximal is used within this specification and the appended claims to refer to the opposite end of the device, typically an end of the handle opposite the blade.

It is known to provide a video display region which is coplanar with the centre line of video laryngoscopes which have generally bilateral symmetry and located at the most proximal end of the laryngoscope handle. For example, this arrangement is known from the products marketed as Pentax AWS-100 and Coopdech C-Scope (Daiken Medical). A disadvantage of these arrangements is that the relatively high mass of the video screen and supporting electronics can provide a relatively large and bulky device in which the centre of gravity is out of the hand and which is harder to manoeuvre than traditional laryngoscopes.

It is also known to provide a video display region which is entirely laterally offset from the handle of a video laryngoscope, and located at the most proximal end of the laryngoscope handle. This is known from the McGrath Series 5 laryngoscope (McGrath is a trade mark of Aircraft Medical Limited). This works well with the laterally offset blade of the laryngoscope but does increase the overall size of the device.

It is known from U.S. Pat. No. 5,827,178 (Berall) to provide a screen located distally on the handle of a video laryngoscope, very close to the blade. However, this design is impractical as it prevents a user from forming a good grip around the blade. The grip is obscured by the screen.

SUMMARY OF THE INVENTION

According to a first aspect of the invention there is provided a video laryngoscope having a body, an insertion section extending from the body generally parallel to a median plane of the laryngoscope extending through the body, and a display screen assembly, the body comprising a grip portion intermediate the display screen assembly and the insertion section. Preferably, the display screen extends generally perpendicular to the median plane. Typically, the display screen extends from the body generally perpendicular to the median plane. The display screen assembly may be mounted to the body. The display screen assembly may at least in part be integral with the body.

Thus the invention extends to a video laryngoscope having a body, an insertion section extending from the body generally parallel to a median plane (for example, parallel to a median plane) of the laryngoscope extending through the body, and a display screen assembly extending from the body generally perpendicular to the median plane (for example, perpendicular to the median plane), the body comprising a grip portion intermediate the display screen assembly and the insertion section.

The invention also extends to a video laryngoscope having a body, an insertion section extending from the body, and a display screen assembly comprising a display screen having an inner edge and an outer edge, the body comprising a grip portion intermediate the display screen assembly and the insertion section;

wherein the laryngoscope has a median plane extending through the body and insertion section and equidistant a first point of maximum lateral extent of the body from a first side of the median plane, and a second point of maximum lateral extent of the body from a second side of the median plane; the display screen assembly extending from the body generally perpendicular to the median plane,
wherein the distance between the outer edge and the median plane is greater than the distance between the first and second points of maximum width and the median plane, and wherein the distance between the inner edge and the median plane is less than the distance between the first and second points of maximum width and the median plane.

The invention extends in a further aspect to a laryngoscope having a body, an insertion section extending from the body generally parallel to a median plane of the laryngoscope extending through the body, and a display screen assembly comprising a display screen having an inner edge and an outer edge, the display screen assembly extending generally perpendicular to the median plane the body comprising a grip portion intermediate the display screen assembly and the insertion section;
wherein the inner edge is within the lateral extent of the body and the outer edge extends beyond the lateral extent of the body, from the median plane. The display screen may extend across the entire lateral extent of the body, with the outer edge extending beyond the lateral extent of the body, at one side of the body, and the inner edge of the display screen extending to the other side of the body.

By the median plane we refer to a virtual plane which will be generally parallel to a patient's midsagittal plane in use, extending through the middle of the lateral extent of the grip portion, when the insertion section is fully inserted into a patient ready for an endotracheal tube to be introduced into the trachea. The laryngoscope is typically not symmetrical through the median plane.

Precise manual control over a laryngoscope, in use, is highly desirable and it is typically necessary, during a medical procedure, for a user (typically a medical practitioner) to be required to make precise changes to the forces applied to the laryngoscope grip, so as to manipulate the tissues of the patient's trachea, larynx or epiglottis. It is also desirable for the structure of a laryngoscope to afford the medical practitioner a satisfactory view of the patient's mouth cavity and, in some cases, a direct view of the tissues being manipulated.

Display screens of known video laryngoscopes may be positioned to one side of the laryngoscope body or on the end of the laryngoscope body, so as to permit the best possible view of the patient's mouth cavity in use (and in some cases permit direct viewing of the patient's trachea, epiglottis or larynx), and so as to afford the user the maximum range of alternative hand positions about the grip and/or the body. Video laryngoscopes are also known having display screens positioned in front of the body, in line with the grip portion, so that the screen is in, or close to, the line of sight of the user when they are directly viewing, thus making alternating between direct and indirect views easier.

Therefore, the display screens which are positioned on the end or to one side of the body are further from the line of sight of the practitioner when they are looking into the patient's oral cavity, making it more difficult to alternate between direct and indirect views, whereas display screens positioned in front of the laryngoscope body inhibit or prevent certain hand positions on the grip, thereby compromising the degree of control available.

Advantageously, the laryngoscope of the present invention is provided with a display screen which is partially in front of, or indented into, or in some embodiments substantially into, the laryngoscope body, such that the screen is positioned close to the line of sight of the practitioner directly viewing the patient's oral cavity, in use, but which does not impede alternative hand grip positions, in particular permitting alternative positions of the user's thumb.

The relative position of the grip portion and the display screen assembly provides further manual control of the laryngoscope; via pressure applied to the surface of the display screen assembly closest to the grip portion.

The insertion section has a proximal end adjoining the body, and a distal end, and the display screen assembly has a first end and a second end, the second end being closer to the insertion section than the first end. In some embodiments, the distance between the second end and the proximate end provides sufficient for the grip portion to be gripped by an adult human hand abutting the second end, in use. Thus, pressure may be applied to the second end (the surface of the display screen assembly closest to the grip portion) without the requirement for the user to move any of the digits of the hand by which the laryngoscope is gripped, in use.

According to a second aspect of the present invention, there is provided a video laryngoscope having a body, an insertion section extending from the body generally parallel to a median plane of the laryngoscope extending through the body, the insertion section having a proximal end adjoining the body, and a distal end;
and a display screen assembly (comprising a display screen) extending generally perpendicular to the median plane, the display screen assembly having a first end and a second end, the second end being closer to the insertion section than the first end; the body comprising a grip portion extending from the second end of the display screen assembly to the proximate end of the insertion section, the distance between the second end and the proximate end sufficient for the grip portion to be gripped by an adult human hand abutting the second end, in use.

Thus, the grip portion is a minimum size to receive an adult human hand, abutting the second end of the display screen assembly. Video laryngoscopes are known having a significant gap between the user's hand (when gripping the grip portion) and the display screen assembly, which are necessarily larger than the laryngoscope of the present invention. Furthermore, it may not be possible to manipulate such known laryngoscopes by applying pressure to a portion (e.g. a second end) of the display screen assembly, or it may be necessary to adjust the position of one or more digits of the hand by which the laryngoscope is being held, in order to manipulate the laryngoscope in this way.

Typically, the display screen has an inner edge and an outer edge and, in some embodiments, the inner edge is within the lateral extent of the body and the outer edge extends beyond the lateral extent of the body, from the median plane.

The body typically extends to a first point of maximum lateral extent from a first side of the median plane, and to a second point of maximum lateral extent from a second side of the median plane, the median plane is equidistant the first and second points. In some embodiments, the display screen has an inner edge and an outer edge, and the distance of the outer edge from the median plane is greater than the distance from the first and second points of maximum lateral extent to the median plane, and wherein the distance from the inner edge to the median plane is less than the distance from the first and second points of maximum lateral extent to the median plane.

Preferably the distance between the proximal end and the second end is between 3 cm and 9 cm.

The width of the average adult human hand (when gripping and object) is between approximately 7.5 cm and 9 cm. Therefore, a distance of at least 3 cm ensures that a user of the laryngoscope is able to encircle the grip portion with at least 2 digits, and a distance of less than 9 cm ensures that the top of a user's hand abuts (or very nearly abuts) the second end, thereby facilitating fine control over the manipulation of the laryngoscope, in use.

The distance may be less than 8.5 cm, or 8 cm. The distance may be greater than approximately 4 cm, or greater than approximately 6 cm, and 9 cm or less, ensuring that the user is able to encircle the grip portion with at least three digits.

In some embodiments, therefore, the distance is such that the user is advantageously able to grip the display screen assembly between a thumb and the forefinger (and in some embodiments the forefinger and/or middle finger), thereby conveying additional control over the manipulation of the laryngoscope.

The proximity of the screen to the insertion section reduces movement of the head by a user looking to and from the screen and the oral cavity.

In some embodiments, the orientation of the screen is adjustable about an axis extending laterally from the body. Advantageously, therefore, the orientation of the screen may be adjusted by the user's thumb, when the user is gripping the grip portion.

In some embodiments, the display screen assembly (and in some embodiments the display screen) may comprise controls. The display screen assembly (and in some embodiments the display screen) of the laryngoscope of the present invention is advantageously positioned so as to enable thumb-operation of such controls during use of the laryngoscope, without the requirement for the user to adjust their grip with the remaining digits of the hand by which the laryngoscope is held. Accordingly, the display screen assembly (and in some embodiments the display screen) may comprise one or more thumb-operable controls.

Alternatively, or in addition, the body may comprise one or more thumb-operated controls.

Accordingly, the invention extends in a third aspect to a video laryngoscope having a body, an insertion section extending from the body generally parallel to a median plane of the laryngoscope extending through the body, a display screen assembly comprising a display screen and extending laterally from the body generally perpendicular to the median plane and a grip portion intermediate the display screen assembly and the insertion section; the body and/or the display screen assembly comprising one or more thumb-operable controls, positioned so as to be operable by a user's thumb without the requirement for the user to adjust their grip with the remaining digits of the hand by which the laryngoscope is held, in use.

The display screen may be a touch screen, and may function as one or more thumb-operable controls.

The or each said thumb-operable control may be operable to control the position, brightness, colour, contrast or other properties of the display screen. The or each said thumb-operable control may be operable to control the position of a moveable element (for example the position of an image capture device) of the insertion section, or the brightness, position or angle of a light source. The or each said thumb-operable control may control the status of the laryngoscope (for example whether the laryngoscope is on or off) or may control a gas supply, or any other suitable function of the laryngoscope, for example, a mechanical function (such as a tube guiding or steering mechanism or other moving part), an optical function or manipulation or control of another device, such as a remote monitor. The thumb control may allow the user to scroll through patient information displayed on the screen or another screen.

The body may comprise the grip portion.

The insertion section may be straight or curved. The insertion section may extend at an angle from the body, or some or all (for example a proximal portion) may extend generally in line with the body. A distal portion of the insertion section may extend at an angle from the remainder (intermediate and/or proximal portions) of the insertion section and/or the body. The insertion section may be integral to the body, or connected to the body and the insertion section may be removably connected, or provided with a removable portion, for example a removable cover.

In use of a laryngoscope, and in particular a video laryngoscope, the body or the display screen assembly may by brought into contact with the patient's chin, neck or chest during a medical procedure.

In some embodiments, the display screen assembly (and the display screen) is flexible (at least in part; typically, at least at its end furthest from the insertion section), so as to minimise possible obstruction by a patient's chin, neck, chest, clothing or other equipment or objects in the vicinity in the event that the display screen assembly is brought into contact therewith. The body may comprise a grip portion and the display screen may be flexible where it extends beyond the grip portion. The grip portion may be rigid. Thus, the screen may flex in use, for example, when it contacts a patient's body or other equipment or objects, beyond the rigid grip portion.

Thus, the invention extends in a further aspect to a video laryngoscope comprising a body, an insertion section extending from the body, and a display screen assembly extending from the body, wherein the display screen assembly is flexible, at least in part (typically, at least at its end furthest from the insertion section). The body may comprise a grip portion and the display screen may be flexible where it extends beyond the grip portion.

The display screen assembly may have a thickness of less than 5 mm (or ⅛ inch). The display screen assembly may be located on the front (user facing) surface of the body. These features mean that it can be tilted further before encountering obstruction.

The display screen assembly may comprise a resilient material, or a resilient member. For example the display screen assembly may comprise a resilient casing which enables (in embodiments having a flexible display screen) the assembly to deform when brought into contact with the patient, and to thereafter return to the original shape. The display screen may comprise and/or be connected to the body by a resilient member, so as to be deflectable (e.g. when brought into contact with the patient's chin, neck or chest, during a medical procedure) and to thereafter return to its original orientation.

The display screen assembly may be integral to the body, or may be connected to the body. The display screen assembly may be pivotable about an axis extending generally perpendicular to the median plane. The display screen may be pivotable about a pivot extending from the body, generally perpendicular to the median plane. The pivot, or at least a portion thereof, may be resilient, such that the display screen assembly may be deflected if it comes into contact with a patient, and thereafter return to its normal orientation.

The display screen is advantageously large, so as to provide the most detailed images to the user. The display screen may comprise all or the majority of the face of the display screen assembly viewable to a user of the laryngoscope during a medical procedure. The display screen preferably has a diagonal dimension above 2.5 cm (1 inches), of greater than 5 cm (2 inches), or at least 6 cm (2.4 inches) or at least 8 cm (3.1 inches). The diagonal dimension may be less than 13 cm (5 inches), less than 12 cm (4.7 inches) or less than 10 cm (3.9 inches). In some embodiments the diagonal dimension is between 8.5-9.0 cm (around 3.5 inches) or 10.0-11.0 cm (around 4.22 inches).

The aspect ratio is typically between 1:1 (height:width) and 2:1 (height:width), more typically between 1.2:1 and 1.8:1, for example around 1.3:1. For example, the aspect ratio may be 4:3, 16:9, 14:9, 8:5, 5:3 or 5:4. The surface area is typically at least 15 cm$^2$ and may be at least 20 cm$^2$. The surface area is typically less than 100 cm$^2$ and may be less than 70 cm$^2$ or less than 60 cm$^2$ or 40 cm$^2$.

It may be that the display screen extends into the clasp of a user's hand when they grip the grip portion.

Preferred and optional features of the any of the above aspects of the invention correspond to preferred and optional features each of the above aspects of the invention.

DESCRIPTION OF THE DRAWINGS

An example embodiment of the present invention will now be illustrated with reference to the following Figures in which:

FIG. 1a is a side view from a first side of a video laryngoscope of the present invention;

FIG. 1b is an end view showing the front face of the display screen assembly of the video laryngoscope of FIG. 1a;

FIG. 1c is a side view from a second side of the video laryngoscope of FIG. 1a;

FIG. 1d is an end view showing the rear face of the display screen assembly; of the video laryngoscope of FIG. 1a;

FIG. 5b is a side view from a first side of the video laryngoscope of FIG. 5a;

FIG. 5c is a top view of the video laryngoscope of FIG. 5a;

FIG. 9b is a perspective view of a second side of the video laryngoscope FIG. 9a;

FIG. 9c is an alternative perspective view of the first side of the video laryngoscope of FIG. 9a;

DETAILED DESCRIPTION OF AN EXAMPLE EMBODIMENT

Figure 2A:
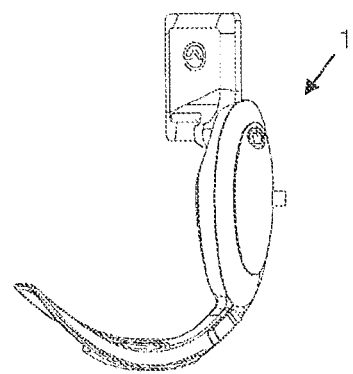
FIG. 2a is perspective view of the video laryngoscope of FIG. 1a-d showing the rear of the display screen assembly, from the second side.
Figure 2B:
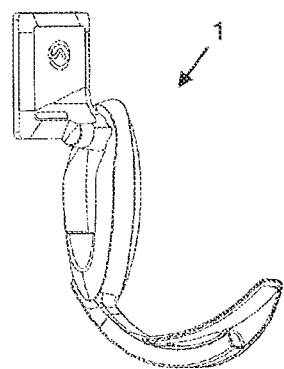
FIG. 2b is perspective view of the video laryngoscope of FIG. 1a-d showing the rear of the display screen assembly, from the first side.
Figure 2C:
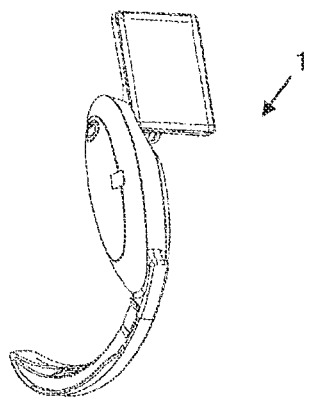
FIG. 2c is perspective view of the video laryngoscope of FIG. 1a-d showing the front of the display screen assembly, from the second side.
Figure 2D:
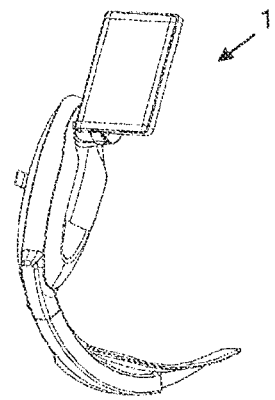
FIG. 2d is perspective view of the video laryngoscope of FIG. 1a-d showing the front of the display screen assembly, from the first side.

FIG. 1 shows a video laryngoscope 1 comprising a body 2 and an insertion section 4 extending from the body. A display screen assembly 8 is connected to the body comprises an LCD display screen 10 which is oriented generally perpendicular to the plane of the insertion section, as can be seen most clearly in FIGS. 1b and 1d.

The insertion section comprises a distal portion 5 for manipulating the tissues of a patient's trachea, epiglottis or larynx, and a camera element 6 extending through a channel in the insertion section to a lens 7. An image obtained by a camera at the distal end of the camera element, adjacent the lens, is operable to capture an image, to be displayed on the screen and thereby provide an indirect view of a patient's oral cavity (and in particular the epiglottis, trachea or larynx) in use.

The insertion section further comprises an inferior surface, which, in use, is engaged with a patient's tongue. The inferior surface of the embodiments shown is provided with a moderate curvature, so as to enable a user of the laryngoscope to directly view the distal tip 14, and thus obtain a direct view of a patient's epiglottis etc., in use.

The display screen assembly is connected to the body and is operable to pivot around axis 16.

The body comprises a grip portion 18, extending from the proximal end 20 of the insertion section, to the edge 22 of the screen assembly which is closest to the axis.

As can be seen in FIGS. 1*b* and 1*d*, the body extends laterally (i.e. in the direction parallel to the screen and generally perpendicular to the insertion section) to a widest point (i.e. of maximum lateral extent) 24, 26 to each of the first and second sides of the body, respectively. The screen has an inner edge 28 and an outer edge 30 and is indented into the body such that the widest point 26 extends laterally beyond the inner edge 28. That is to say, as measured from a notional plane A, which extends perpendicular to the screen and parallel to the insertion section, through the body, equidistant the widest point 24, 26 of the body, the inner edge 28 is closer to A than the widest points 24, 26 of the body, and the outer edge 30 is further from A than the widest points 24, 26 of the body.

Perspective view of the laryngoscope 1, showing the features discussed above, are show in FIGS. 2*a-d*.

In use, the laryngoscope 1 is gripped around the grip portion. The grip portion is sized to receive an adult human hand (the length of the grip portion, i.e. the distance in the plane A between the proximal end of the insertion section and the end 22 of the screen assembly being 9 cm).

Thus, the body is only as large as is necessary to allow the user to grip the grip portion with all of the digits of the hand by which the laryngoscope is gripped. Additionally, the user's hand will necessarily abut the end 22 of the display screen assembly, such that pressure may be applied to the end 22 without changing grip (or by changing grip minimally) so as to facilitate precise manipulation of the laryngoscope during a medical procedure, by applying pressure or leverage to the end 22 of the display screen assembly.

Furthermore, minimising the length of the grip ensures that the screen is as close as possible to the line of sight of the user when directly viewing the distal tip 14, so that alternating between a direct view and the indirect view displayed on the screen, is as convenient as possible.

Positioning of the display screen assembly indented, but not fully covering, the end portion 32 of the body, places the screen close enough to the grip portion that the angle of the screen may be adjusted by the user's thumb without changing grip with the remaining digits, whilst leaving the end portion exposed such that pressure may be applied by the user's thumb so as to manipulate the laryngoscope during a medical procedure.

In alternative embodiments (not shown) a power switch (or other control) is also provided on the end portion of the body, such that the laryngoscope may be controlled (for example the camera activated) by the user, without the need to change the grip of the remaining digits by which the laryngoscope is held. Thus, the video features (or other features) of the laryngoscope may be controlled more effectively during a medical procedure.

Figure 3A:
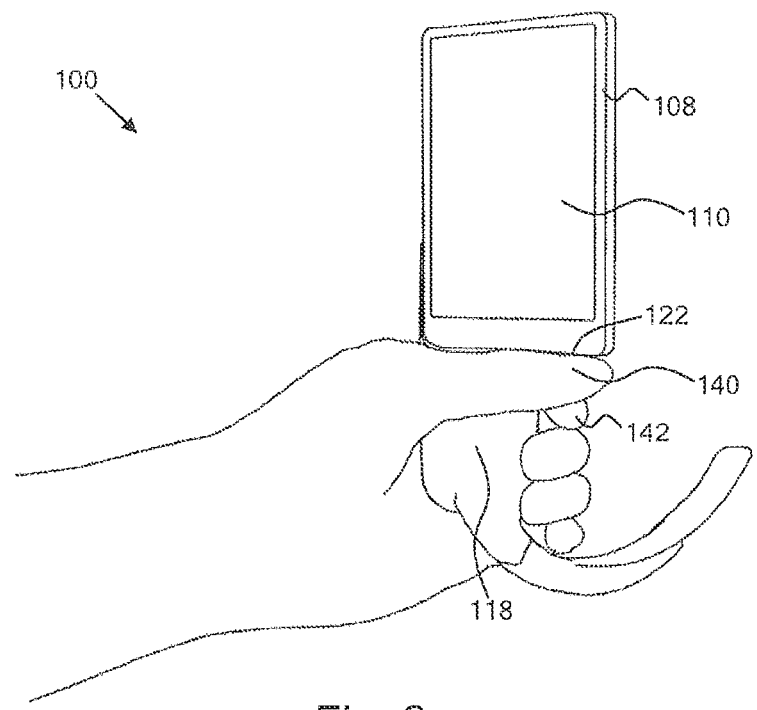
FIG. 3a is perspective view of an alternative embodiment of a front side of the video laryngoscope of the invention, gripped by an adult human hand.
Figure 3B:
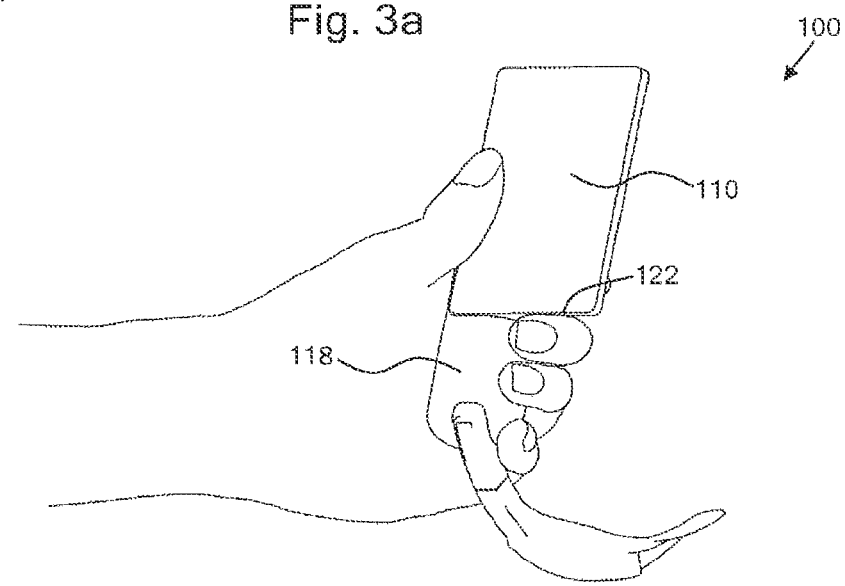
FIG. 3b is perspective view of a back side of the video laryngoscope of FIG. 3a, gripped by an adult human hand.
Figure 4A:
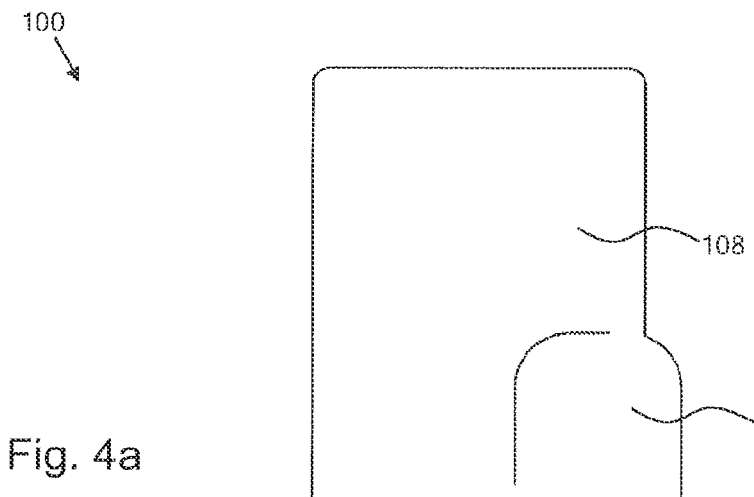
FIG. 4a is an end view of the video laryngoscope of FIGS. 3a and 3b, gripped by an adult human hand.
Figure 4B:
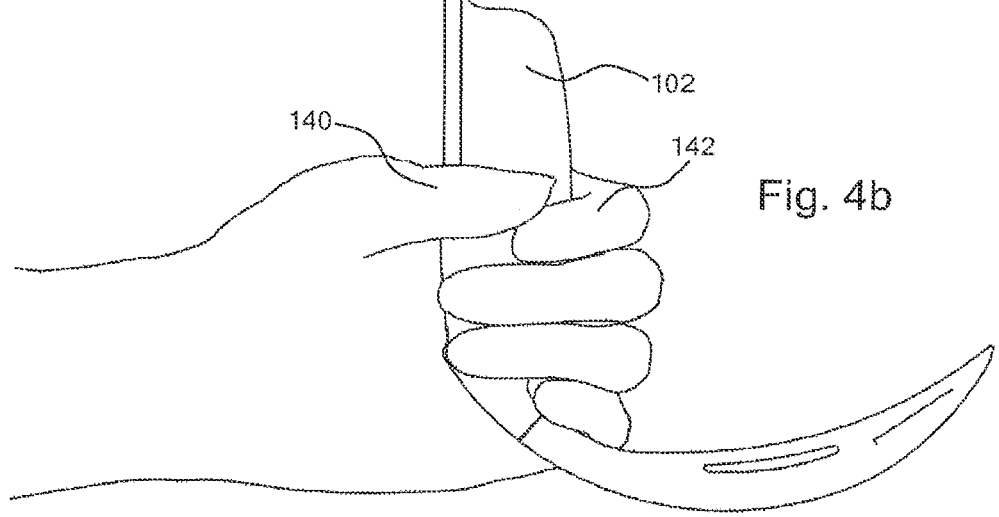
FIG. 4b is a side view of the video laryngoscope of FIGS. 3a and 3b, gripped by an adult human hand.

FIGS. 3 and 4 show an alternative embodiment of a laryngoscope 100 of the present invention differing only from laryngoscope 1 in having a larger screen assembly 108 which is co-moulded with the body 102. The body (comprising grip portion 118) is of similar dimensions to the body 1 of laryngoscope 1, and the grip portion of the body 102 also has a length of 9 cm. As show in FIGS. 3*a*, 4*a* and 4*b*, the grip portion is large enough to be encircled by an adult human hand, with the thumb 140 and forefinger 142 abutting the edge 122 of the screen assembly, thus facilitating the manipulation of the laryngoscope during a medical procedure (via leverage applied to the edge 122) without, or with minimal, changes to the user's grip.

Display screen 110 is a touch screen, comprising thumb-operable controls (as shown in FIG. 3*b*). The position of the screen in relation to the grip portion, as discussed above, enables operation of the display screen parameters during a medical procedure.

FIGS. 5*a-d* shows various views of a further embodiment of a laryngoscope 200 of the present invention.

In certain circumstances, it is advantageous for the entire laryngoscope to be compact. For example, a smaller device may be more easily stored, for use by paramedics. In particular also, small laryngoscopes are adapted for use with smaller patients such as children or infants. It is additionally beneficial for the screen assembly to be of reduced size, so as to reduce contact with the chin, neck or chest of a smaller patient.

Accordingly, laryngoscope 200 (of FIGS. 5 and 6) is provided with a comparatively small screen assembly 208 and a grip portion 218 of 5 cm length. The insertion section 204 is of correspondingly reduced size in comparison to the embodiments discussed above.

Figure 5A:
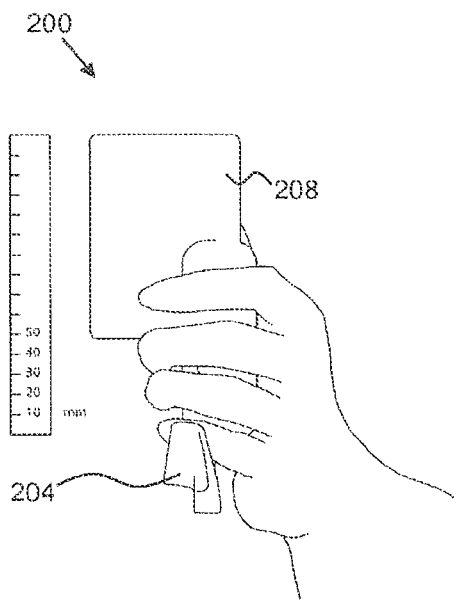
FIG. 5a is an end view showing the rear face of the display screen assembly of a video laryngoscope of the present invention.
Figure 5B:
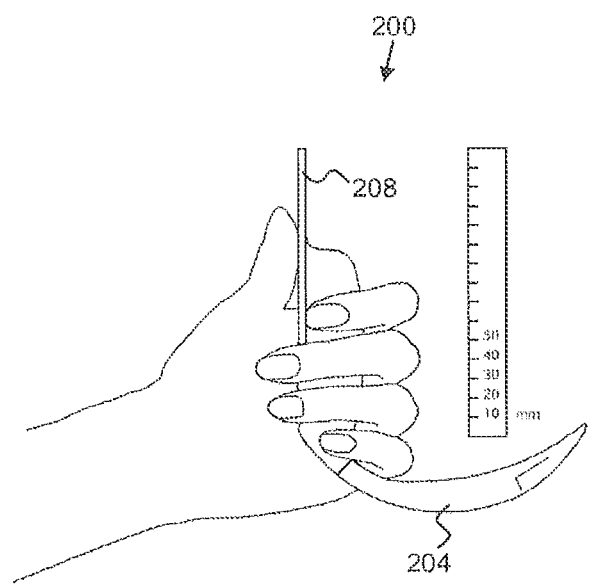
Figure 5C:
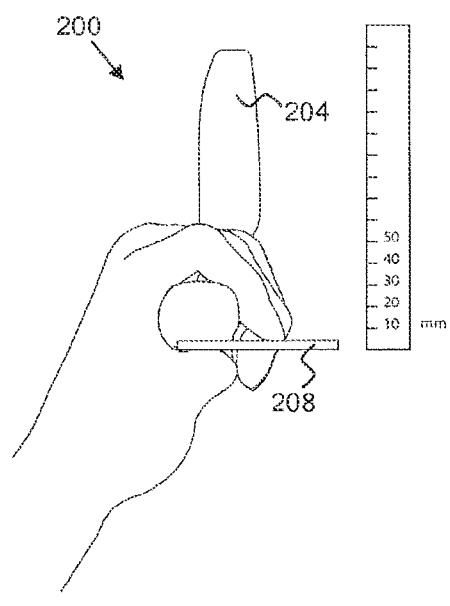
Figure 5D:
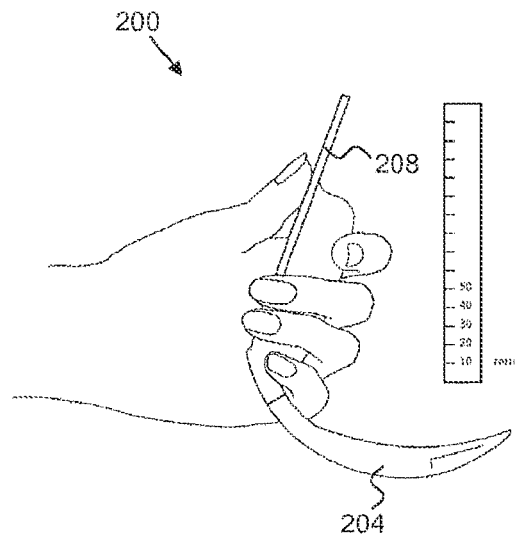
FIG. 5d is a side view from a second side; of the video laryngoscope of FIG. 5a, gripped by an adult human hand.
Figure 6A:
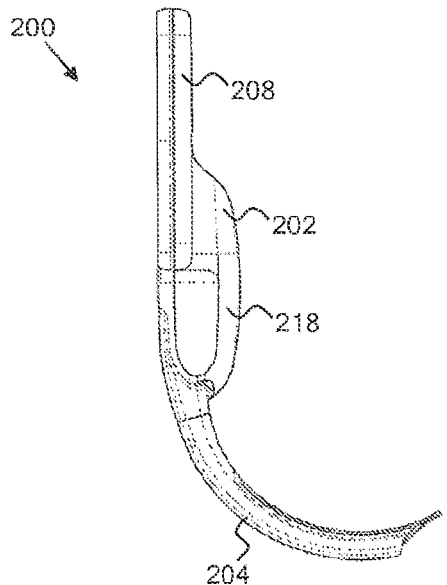
FIG. 6a is a side view of the video laryngoscope of FIG. 5.
Figure 6B:
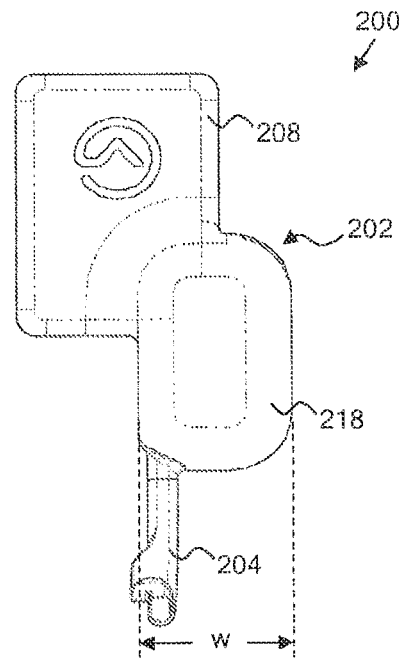
FIG. 6b is an end view showing the rear face of the display screen assembly of the video laryngoscope of FIG. 5.
Figure 6C:
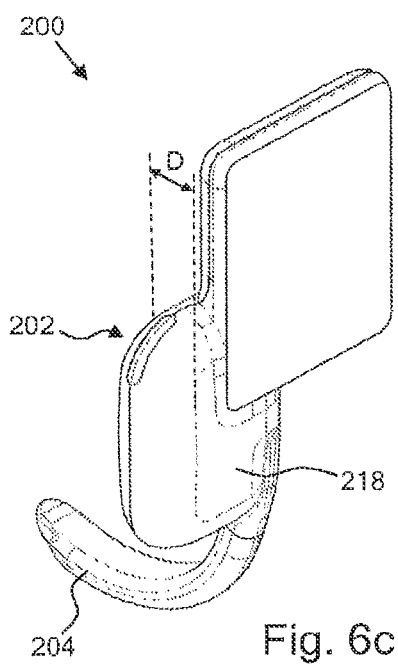
FIG. 6c is a perspective view showing the rear face of a first side of the display screen assembly; of the video laryngoscope of FIG. 5.
Figure 6D:
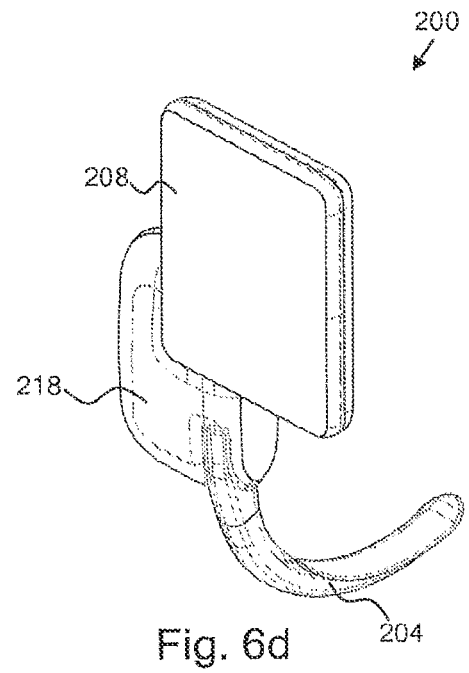
FIG. 6d is a perspective view showing the rear face of a second side of the display screen assembly; of the video laryngoscope of FIG. 5.
Figure 7A:
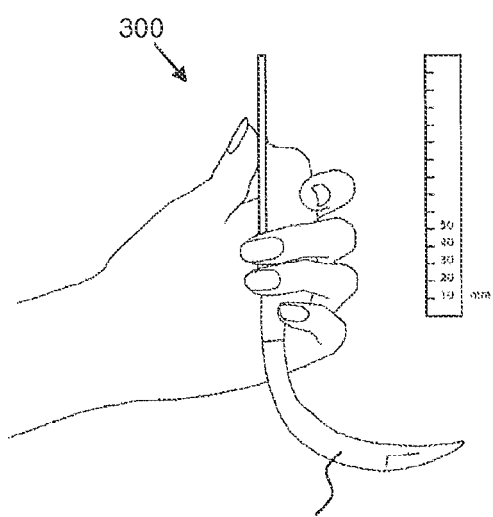
FIG. 7a is a side view of a video laryngoscope of the present invention being gripped by an adult hand.
Figure 7B:
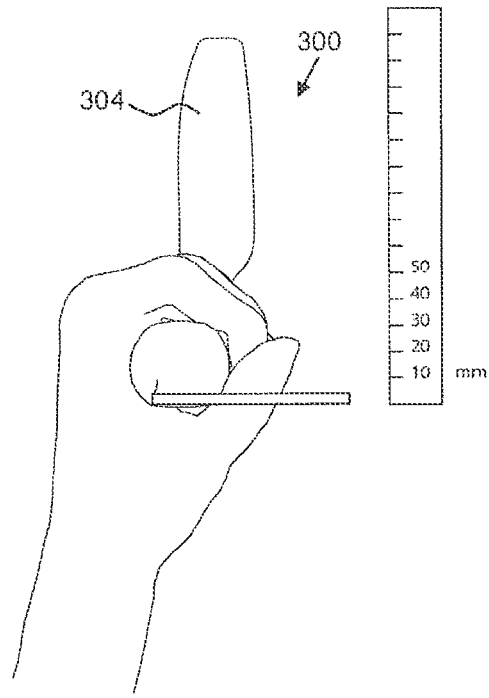
FIG. 7b is a plan view; of the video laryngoscope being gripped by an adult hand.
Figure 7C:
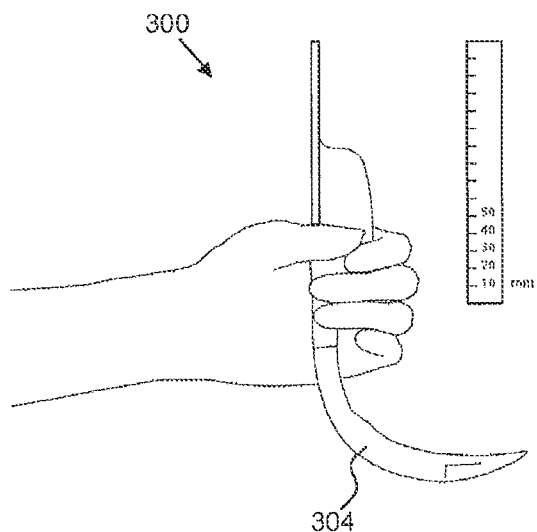
FIG. 7c is a side view of an alternative hand grip position of the video laryngoscope.
Figure 7D:
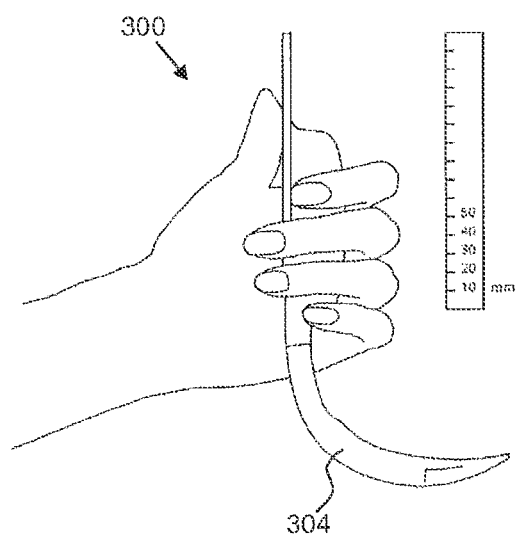
FIG. 7d is a side view of a further alternative hand grip position; of the video laryngoscope.
Figure 8A:
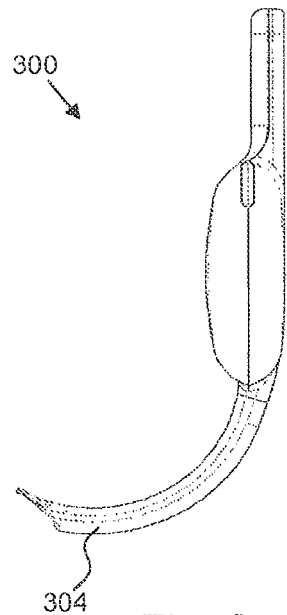
FIG. 8a is a side view of the video laryngoscope of FIG. 7.
Figure 8B:
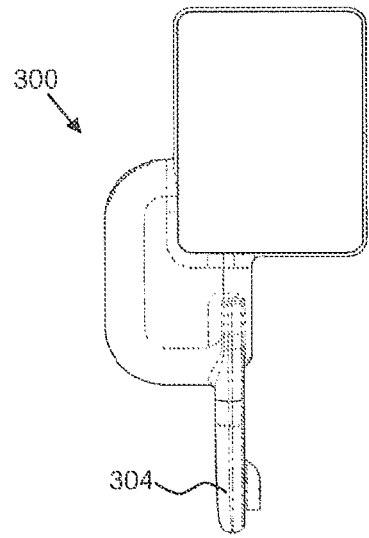
FIG. 8b is an end view showing the rear face of the display screen assembly of the video laryngoscope of FIG. 7.
Figure 8C:
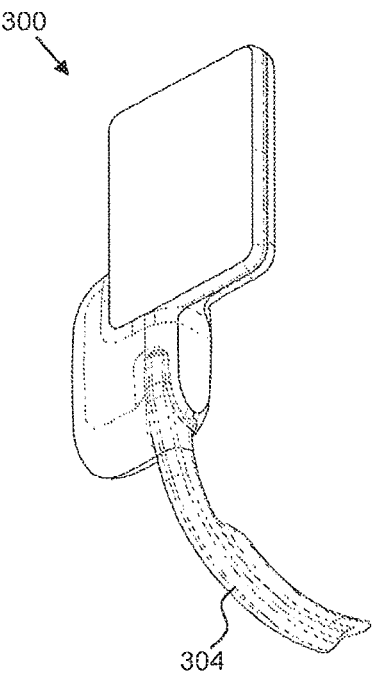
FIG. 8c is a perspective view showing the rear face of the display screen assembly; of the video laryngoscope of FIG. 7.
Figure 8D:
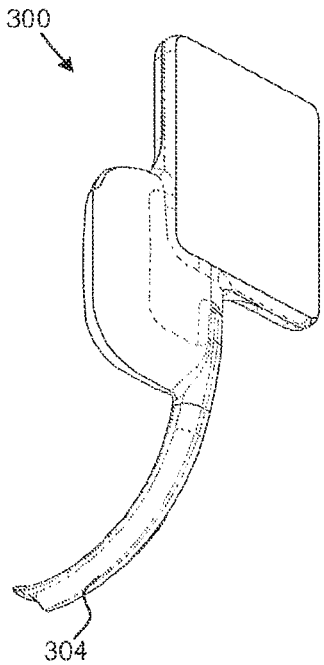
FIG. 8d is a perspective view showing the rear face of the display screen assembly; of the video laryngoscope of FIG. 7.
Figure 9A:
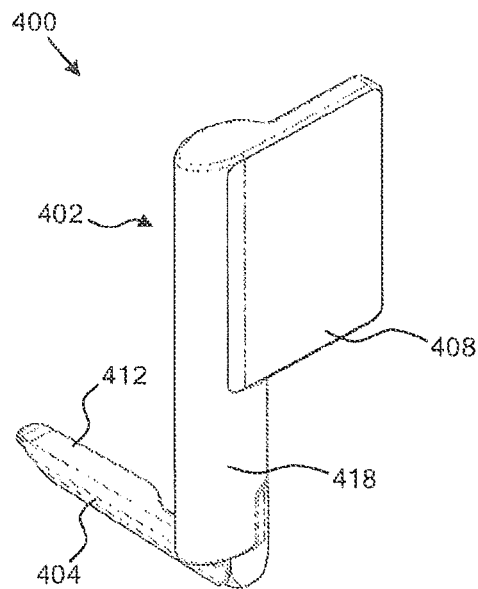
FIG. 9a is a perspective view of a first side of a video laryngoscope of the present invention.
Figure 9B:
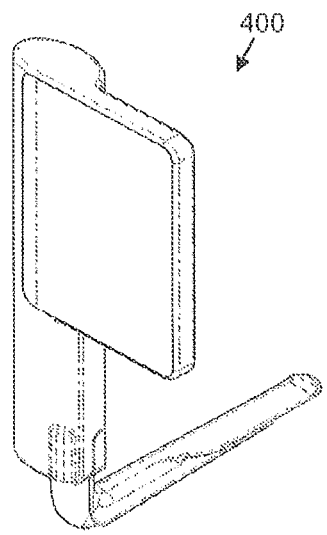
Figure 9C:
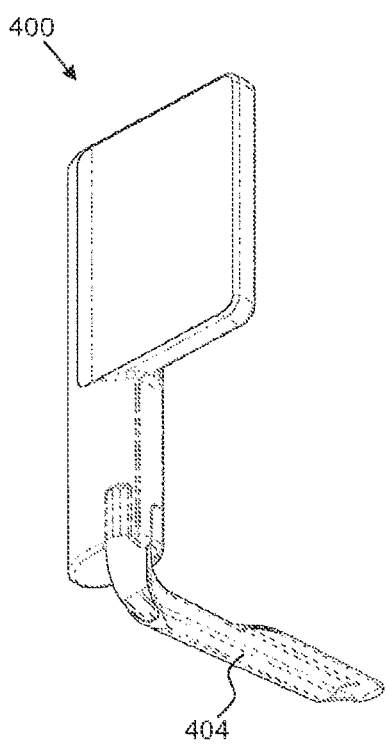
Figure 9D:
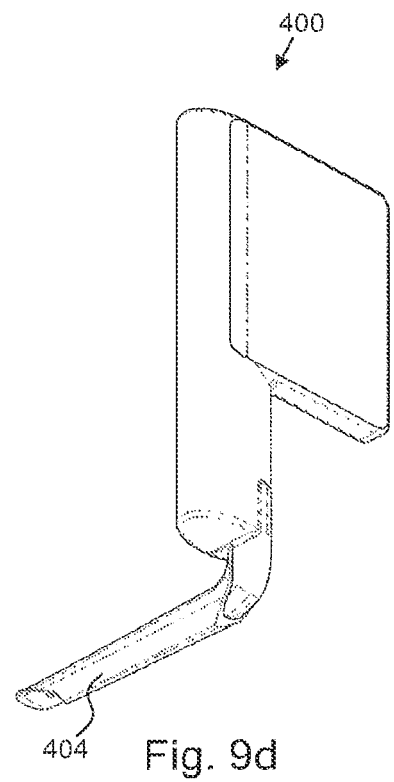
FIG. 9d is an alternative perspective view of the second side of the video laryngoscope FIG. 9b.
Figure 10A:
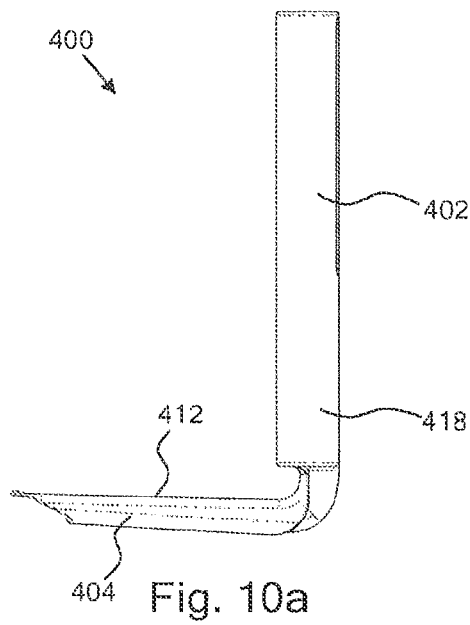
FIG. 10a is a side view of the video laryngoscope of FIG. 9.
Figure 10B:
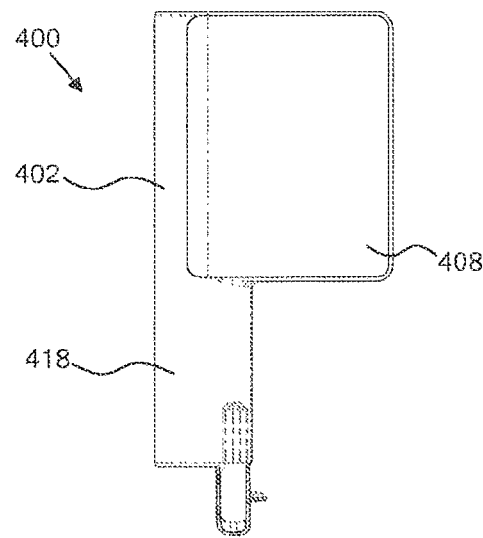
FIG. 10b is an end view of the video laryngoscope of FIG. 9.
Figure 10C:
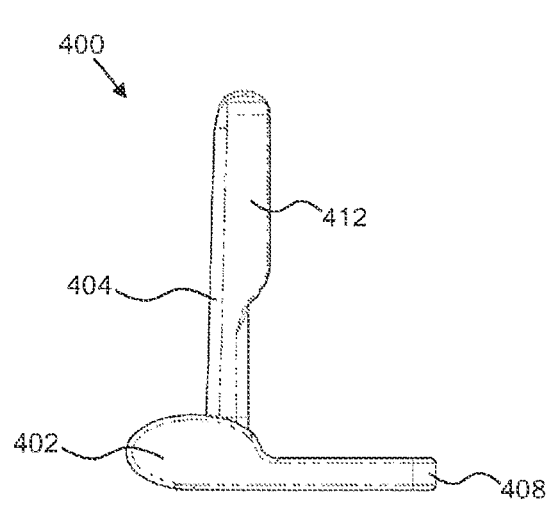
FIG. 10c is a plan view with the display screen assembly foremost of the video laryngoscope of FIG. 9.
Figure 10D:
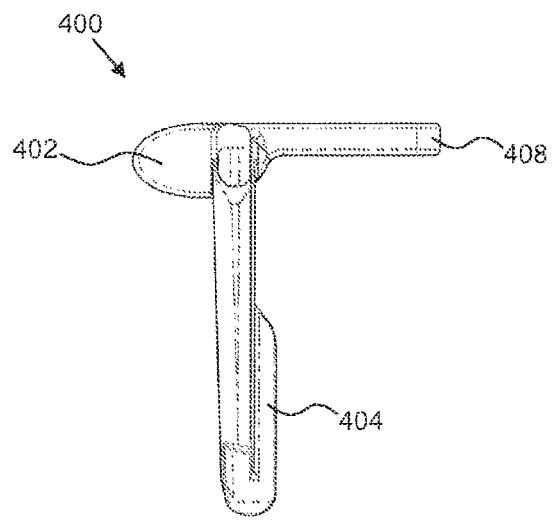
FIG. 10d is a plan view showing the insertion section foremost; of the video laryngoscope of FIG. 9.

The body 218 has a greater width W than depth D. A body having a maximum lateral extent greater than the maximum extent of the body perpendicular to the plane of the display screen may advantageously be gripped in a different manner to handles having generally round or rounded-rectangular profiles. For example, hand grip positions wherein the display screen assembly and/or the body are gripped or leveraged between the thumb and forefinger (for example as shown in FIGS. 5*b* and 7*d*) may be more readily achieved. Some users may have a preference for certain grip positions, (for example leveraging or "pinching" between the thumb and forefinger) for example users with smaller hands. Similarly, some grip positions may be more appropriate for certain types of medical procedure.

The body may have a maximum lateral extent that is between one and two times the maximum extent perpendicular to the plane of the display screen, or between one and three times, or between two and three times, or greater than three, or four times.

In addition, a "flattened" body profile, such as the profile of body 218 enables longitudinal extent (i.e. the height) of the laryngoscope to be reduced, e.g. for ease of storage or use with infants.

The grip portion (which can be more clearly seen in FIG. 6) is of sufficient size to be encircled by three digits of an adult human hand.

FIGS. 7, 8, 9 and 10 show further embodiments of the present invention. Laryngoscope 300 is sized similarly to laryngoscope 200, but is provided with an alternative insertion section 304, having a different curvature and extending at a different angle from the body, than the insertion section 204 of laryngoscope 200.

Laryngoscope 400 is a further embodiment of the invention, showing an alternative shape of grip portion 418, body 402 and screen assembly 408 extending laterally from the body. Laryngoscope 400 is specifically adapted for optimal direct viewing and is provided with a straight insertion section 404, having a generally flat inferior surface 412.

Figure 11:
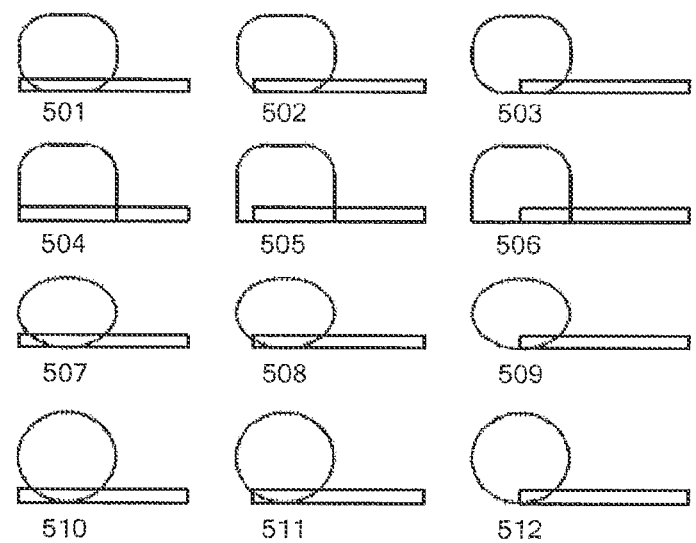
FIG. 11 shows schematic plan views of laryngoscope configurations, showing alternative body shapes and display screen assembly positions.

FIG. 11 shows schematic plan views of laryngoscope configurations, showing alternative body shapes and display screen assembly positions. Each figure depicts the maximum lateral extent of the display screen assembly and the body, as viewed along an axis parallel to the median plane and the plane of the display screen.

The laryngoscope body may be provided with a rounded rectangular profile having all four corners rounded (configurations 501, 502 and 503) or having the two corners furthest from the face of the display screen rounded (configurations 504, 505 and 506). The laryngoscope body may be provided with an oval profile, wherein the long axis of symmetry of the oval generally parallel to the plane of the display (configurations 507, 508 and 509), or with a circular profile (configurations 510, 511 and 512).

The display screen assembly may extend to the same lateral extent as the body to the first side of the median plane (such that the body extends laterally beyond the display screen itself), and beyond the maximum lateral extent of the body to the second side of the median plane (configurations 501, 504, 507 and 510). The body may extend laterally beyond the display screen assembly (and thus the display screen) to the first side, and the display screen assembly may extend laterally beyond the body (configurations 502, 503, 505, 506, 508, 509, 511 and 512). In some embodiments, for example where the display screen assembly is inset into the body and pivotable, the display screen assembly extends from approximately in line with the median plane (configurations 503, 506, 509 and 512).

The embodiment shown in FIGS. 1 and 2 is configured generally as laryngoscope 512. The embodiments shown in FIGS. 4, 5 and 7 are configured generally as laryngoscope 502. The embodiments shown in FIGS. 6 and 8 are configured generally as laryngoscope 503, and the embodiment shown in FIGS. 9 and 10 is configured generally as laryngoscope 508.

Human hands differ in size and strength. Laryngoscope bodies of different profiles have different ergonomic properties and some users may prefer one body shape over another, and may find manipulation of a laryngoscope having a certain body shape or size easier than other shapes/sizes. The lateral extension of the screen assembly from the body may also be important, as different lateral extension changes the extent to which the assembly may be pinched or leveraged, in use, and therefore some users may prefer or be better able to manipulate a laryngoscope having a certain configuration.

Figure 12:
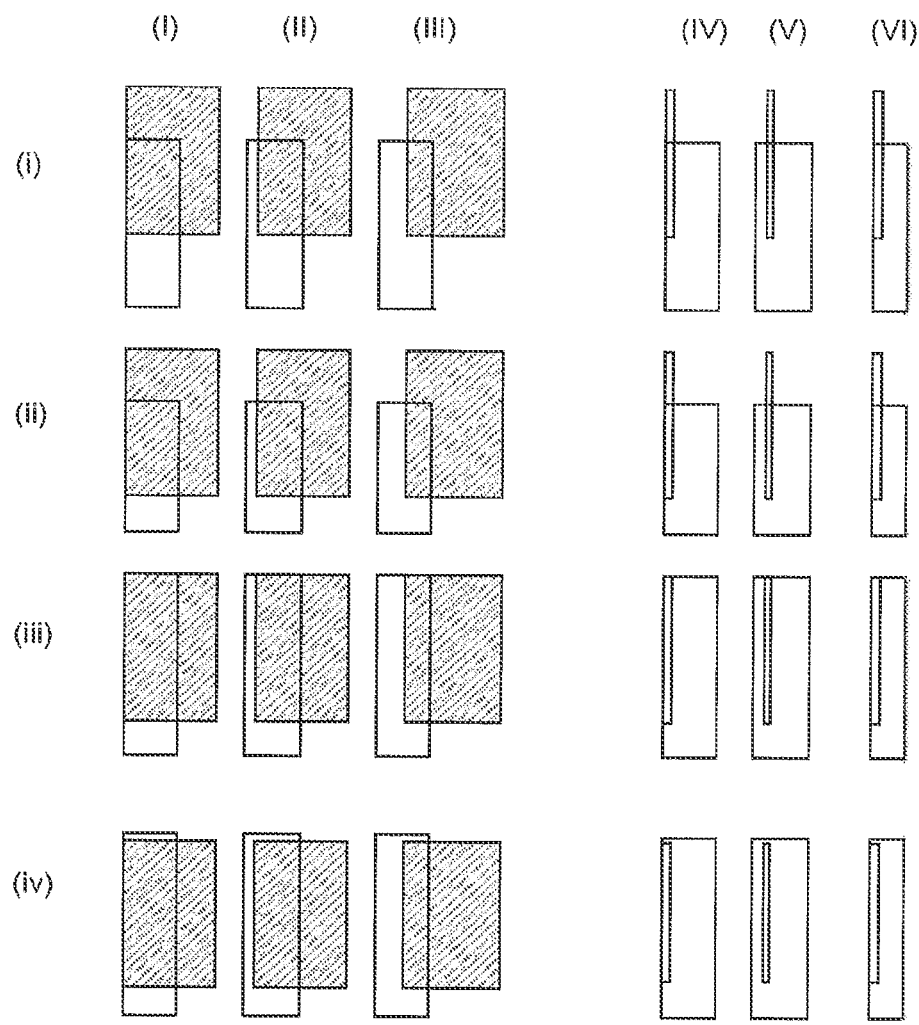
FIG. 12 shows schematic face and side views of laryngoscope configurations, showing alternative relative positions of body and screen.

FIG. 12 shows an array of alternative configurations of laryngoscope body and screen. The maximum lateral extent of the body (unshaded rectangle) and display screen assembly (shaded rectangle) is shown in the face views of configurations in columns (I), (II) and (III). The maximum depth and relative positions out of the plane of the display screen, of the display screen assembly and laryngoscope body are shown in the side views (i.e. parallel to the plane of the display screen) in the configurations shown in columns (IV), (V) and (VI). A laryngoscope of the present invention may have a configuration according to any of columns (I)-(III) in combination with any of columns (IV)-(VI). The display screen and the body of a laryngoscope of the present invention may occupy substantially all of the volumes so defined, or only a part.

For example, a body having a round or oval profile (such as laryngoscopes having configurations 507 to 512, shown in FIG. 11) may have the same maximum lateral extent and depths a bodies having rounded rectangular profiles (such as laryngoscopes having configurations 501 to 506). The display screen assembly and, more typically, the body, may be tapered in one, two, or three dimensions, such as the body of the laryngoscope shown in FIGS. 1 and 2.

As also shown in FIG. 11, the display screen assembly may extend to the same lateral extent as the body to the first side of the median plane (such that the body extends laterally beyond the display screen itself), and beyond the maximum lateral extent of the body to the second side of the median plane (column (I)). The body may extend laterally beyond the display screen assembly (and thus the display screen) to the first side, and the display screen assembly may extend laterally beyond the body (columns (II) and (III)). In some embodiments, the display screen assembly extends from approximately in line with the median plane (column (III)).

The display screen assembly may extend longitudinally beyond the body (configurations shown in rows (i) and (ii)), or the maximum longitudinal extent of the display screen assembly and the body from the laryngoscope blade (and handle portion) may be in line with each other (configurations shown in row (iii)) or the body may extend longitudinally beyond the display screen assembly (configurations shown in row (iv)).

The relative longitudinal extent of the body and the display screen assembly may vary, so as to provide handle portions of different lengths (e.g. to allow the handle to be gripped by all of the fingers of an adult human hand, or by only two or three). For example, the configurations of row (i) are similar to those shown in row (ii), but the body has a greater longitudinal extent and thus a longer handle portion. Further configurations (for example long-handle configurations corresponding to those show in rows (iii) and (iv)) are also envisaged.

Further variations and modifications fall within the scope of the invention herein disclosed.

The invention claimed is:

1. A video laryngoscope comprising:
   a body, wherein the body comprises a grip portion having an oval profile comprising a long axis and a short axis, wherein the long axis is generally perpendicular to a median plane of the body,
   a display screen assembly extending from the body along a plane substantially perpendicular to the median plane, wherein:
   the display screen assembly comprises a display screen having an inner edge and an outer edge, and
   the inner edge is within a lateral extent of the body on a first side of the median plane and the outer edge extends beyond the lateral extent of the body on an opposing side of the median plane.

2. The video laryngoscope of claim 1, wherein the lateral extent of the body comprises a tapered indent that axially tapers on a first side of the grip portion towards a proximal end of the body.

3. The video laryngoscope of claim 1, wherein dimensions of the long axis and short axis of the oval profile change between a proximal end and a distal end of the body.

4. The video laryngoscope of claim 1, wherein the body is tapered in multiple dimensions.

5. The video laryngoscope of claim 1, wherein the long axis is substantially perpendicular to an axis extending between a proximal end and a distal end of the body.

6. The video laryngoscope of claim 1, wherein the body comprises a power switch on a side of the body opposite to the display screen assembly.

7. The video laryngoscope of claim 1, wherein the display screen is pivotably coupled to the body.

8. A video laryngoscope comprising:
a body comprising a proximal end and a distal end, wherein the body comprises a grip portion having an oval profile having a long axis and a short axis, wherein the body extends from the proximal end to the distal end,
a camera element coupled to the body and extending from the distal end of the body, and
a display screen assembly positioned at or near the proximal end of the body, wherein the display screen assembly comprises a display screen having a first vertical edge and a second vertical edge, wherein a first imaginary axis along the first vertical edge passes through the body and the first imaginary axis is substantially parallel with the long axis, wherein at least a portion of the display screen is integral with the body.

9. The video laryngoscope of claim 8, wherein the grip portion tapers along the long axis, the short axis, or both.

10. The video laryngoscope of claim 8, wherein the display screen is pivotably coupled to the body.

11. The video laryngoscope of claim 8, wherein the display screen extends from the body along a plane substantially parallel to the long axis.

12. The video laryngoscope of claim 8, wherein the long axis is perpendicular to a median plane of the body.

13. The video laryngoscope of claim 8, further comprising a removable blade, wherein the camera element is positioned within the removable blade.

14. The video laryngoscope of claim 8, wherein the first imaginary axis along the first vertical edge passes through the body on a first side of a median plane of the body, and wherein a second imaginary axis along the second vertical edge on an opposing side of the median plane does not pass through the body.

15. The video laryngoscope of claim 8, wherein the first vertical edge of the display screen is substantially parallel to a median plane of the body.

16. A video laryngoscope comprising:
a body comprising a proximal end and a distal end, wherein the body extends from the proximal end to the distal end along a median plane of the laryngoscope body, and wherein the body comprises an oval profile that is substantially perpendicular to the median plane, wherein the oval profile comprises a short axis and a long axis; and
a display screen positioned at or near the proximal end of the body, the display screen comprising an inner edge and an outer edge, wherein at least a portion of the display screen is integral with the body, wherein the inner edge is positioned within a tapered indent of the body, and wherein the inner edge is substantially perpendicular to the long axis.

17. The video laryngoscope of claim 16, wherein the body tapers in multiple dimensions.

18. The video laryngoscope of claim 16, wherein the display screen extends longitudinally beyond the body in a direction away from the proximal end.

19. The video laryngoscope of claim 16, wherein the body tapers along the short axis towards the proximal end, the distal end, or both.

20. The video laryngoscope of claim 16, wherein the tapered indent axially tapers along the long axis.

* * * * *